United States Patent [19]

Kagan

[11] 4,391,274

[45] Jul. 5, 1983

[54] FILTERED HUB DEVICE FOR ASPIRATING AND INJECTING LIQUIDS

[75] Inventor: Jonathan Kagan, Fairview, Pa.

[73] Assignee: Becton, Dickinson and Company, Paramus, N.J.

[21] Appl. No.: 277,475

[22] Filed: Jun. 26, 1981

[51] Int. Cl.³ .............................................. A61M 5/00
[52] U.S. Cl. .................................................... 604/190
[58] Field of Search .......... 128/218 N, 218 NV, 274, 128/215, 216, 220, 221, 272.3

[56] References Cited

U.S. PATENT DOCUMENTS 4,066,079  1/1978  Chiarolla ..................... 128/218 N
4,332,249  6/1982  Joslin .......................... 128/218 NV

*Primary Examiner*—John D. Yasko
*Attorney, Agent, or Firm*—Richard J. Rodrick

[57] ABSTRACT

A hub device for use in transferring liquids therethrough in opposite directions includes a housing having an internal chamber and two openings communicating with the chamber. A filter is in the chamber and is adapted to filter particulate matter from liquids. A dual-element valve allows liquid flowing through the chamber from one of the openings toward the other to pass through the filter in one direction of flow, but not the other.

1 Claim, 5 Drawing Figures

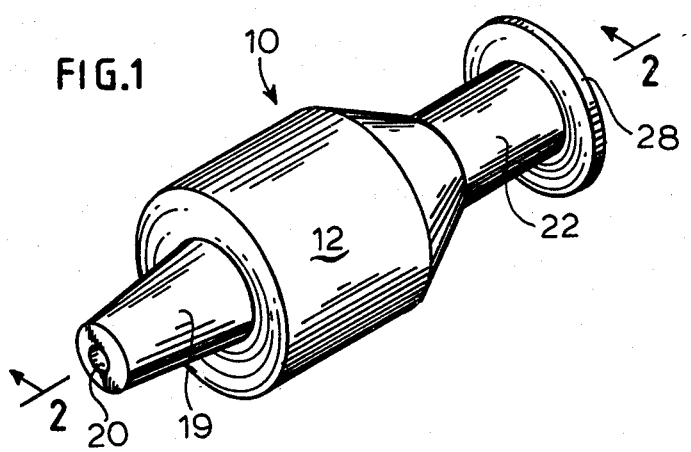
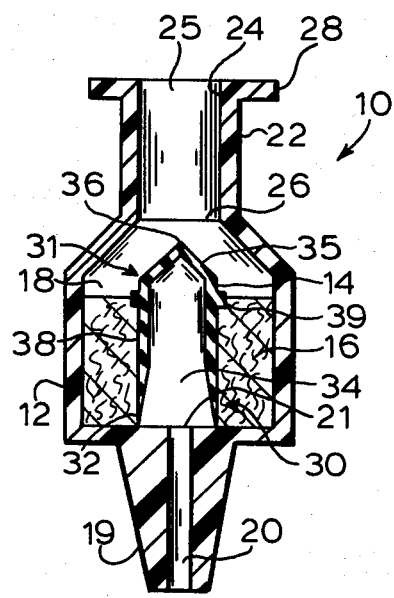
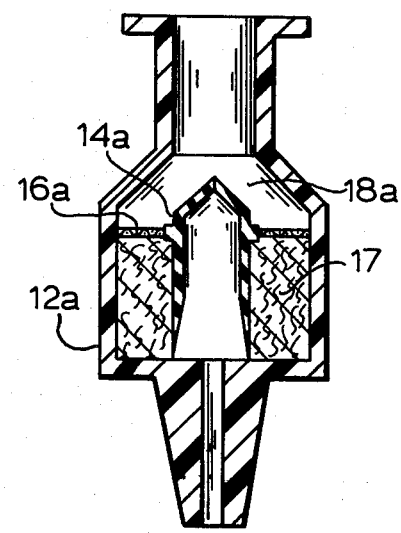

FILTERED HUB DEVICE FOR ASPIRATING AND INJECTING LIQUIDS

BACKGROUND OF THE INVENTION

1. Field of the Invention

The present invention relates to a hub device for use in transferring liquids therethrough in opposite directions, and more particularly, concerns a filtered hub device for aspirating and injecting liquids, such as liquid medications.

2. Description of the Prior Art

In the procedure of transferring a liquid from one source to another, especially when the purity, cleanliness or sterility of the liquid must be preserved, care must be taken to prevent contamination of the liquid during the transfer stages. In particular, many medical liquids are stored in containers or bottles holding a large quantity of the medical liquid. Small amounts of the liquid are withdrawn, for example, into a syringe by aspirating the liquid through a hollow cannula or the like attached to the syringe. To assure that clean or filtered liquid is withdrawn from the larger container, a cannula with a filter may be attached to the syringe during the aspirating process. Such a filter-type cannula is described in U.S. Pat. No. 4,127,131. Before the liquid collected into the syringe is ejected, such as by injecting the liquid into a patient or another container for perhaps additional testing, the filter cannula is generally removed and another similar filter cannula is required. Thus, two such filtered cannulae are often required in this type of liquid transfer procedure: one for aspirating, and another one for injecting the liquid. This, of course, assures filtration of the liquid in both directions, but also requires not only two separate filter cannulae, but also the extra procedural steps of removal and replacement of the cannula. On the other hand, if no filtration is necessary during the aspirating step, the standard aspirating syringe could be used without a filter-type cannula attached thereto. Then, the user would only have to attach the filter cannula before the injection step to assure that filtration of the liquid occurs during this step. In this case, however, the user must remember to place the cannula onto the syringe between the steps of aspiration and injection of the liquid which is being transferred. Should the user forget this intermediate step, then no filtration of the liquid will occur during the entire transfer operation. Therefore, it is desirable to provide an attachment device, particularly suitable for, but not limited to, syringes, which is attachable prior to aspiration of the liquid from the first source and which remains attached to provide a filtration mechanism when the liquid is injected from the syringe to the transferred location. It is to this end which the present invention is directed.

SUMMARY OF THE INVENTION

The hub device of the present invention is useful in transferring liquids therethrough in opposite directions. This hub includes a housing having a chamber therein and two openings communicating with the chamber. A filter is in the chamber adapted to filter particulate matter from liquids passing therethrough. Means is included for allowing liquid flowing through the chamber from one of said openings toward the other to pass through the filter in one direction of flow, but not the other.

In a preferred embodiment of the present invention, the hub device is useful in aspirating and injecting liquids. The first opening in the housing is for aspirating liquid into the chamber and for injecting liquid out of the chamber. The second opening extends through a mouth portion which is adapted to connect to a mating portion of a syringe device which serves as a driving force for aspirating liquid into and injecting liquid out of the device. A dual-element operable valve is positioned in the chamber with the operable elements on opposite ends thereof, the first operable element associated with the first opening, with the second operable element facing toward the second opening of the housing. During aspiration of liquid into the chamber through the first opening the first valve element is adapted to close and then open during injection of liquid into the chamber through the second opening. On the other hand, the second valve element is adapted to open during aspiration of liquid inwardly through the first opening and close upon injection of liquid into the chamber through the second opening. With this structure, liquid passes through the filter in the chamber only during injection of liquid into the chamber when the second valve element is closed and the first valve element is open.

In accordance with the principles of the present invention, many advantages are offered. In particular, the hub device of the present invention may be attached to a syringe-type device before liquid is aspirated into the syringe, and remain attached during injection of the liquid from the syringe while also filtering the liquid as it is being injected. Not only is contamination minimized by filtering the liquid as it is being injected, but the present invention also eliminates the need to either replace or add filter devices between the aspiration and injection steps. As a result, fewer manipulative steps are required by the user of a syringe which includes the hub device of the present invention. Overall, use of the hub device of the present invention provides a simplified procedure for transferring liquid from one location to another, without compromising the cleanliness or purity of the originally collected liquid.

BRIEF DESCRIPTION OF THE DRAWINGS

FIG. 1 is a perspective view of the preferred embodiment of the hub device of the present invention;

FIG. 2 is a cross-sectional view of the hub device taken along line 2—2 of FIG. 1;

FIG. 3 is a cross-sectional view similar to that of FIG. 2, but illustrating an alternate embodiment of the filter inside the hub chamber;

DETAILED DESCRIPTION

Figure 4:
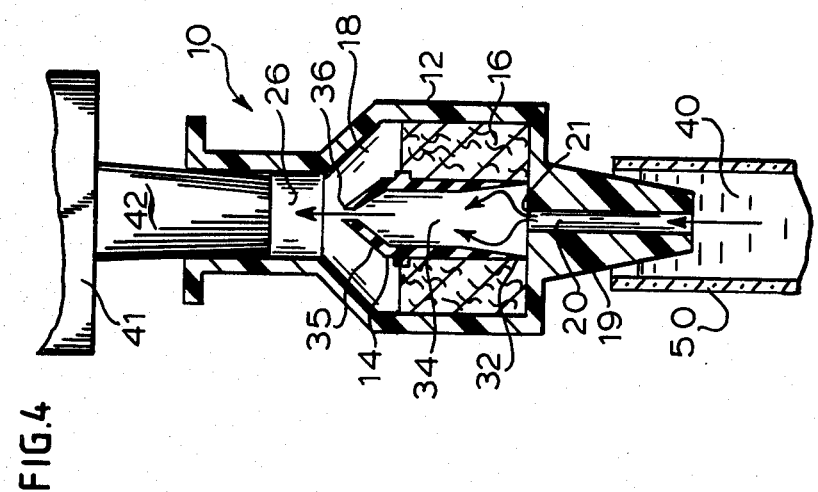
FIG. 4 is a cross-sectional view of the hub device of FIG. 1 illustrating its use during the aspiration step in conjunction with a syringe.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Referring now to the drawings, and FIGS. 1 and 2 in particular, there is illustrated the preferred hub device 10 of the present invention which is particularly useful in aspirating and injecting liquids. This hub device is comprised of only a few basic components: a generally cylindrical housing 12, an operable valve 14 and a filter element 16, both the valve and filter element being inside the housing.

More particularly, housing 12 is a preferably rigid structure formed with a chamber 18 therein. Protruding from one side of the housing is a narrow, tapered extension 19 which includes a passageway 20 therethrough. An opening 21 at the end of passageway 20 provides fluid communication between the passageway and the chamber inside the housing. Extension 19 is preferably tapered so that it may conveniently mate with standard female-tapered hubs well known and used on a variety of cannula, catheter or similar liquid transfer devices. If desired, the outside surface of extension 19 could be threaded to provide for a threaded connection to a mating connector. Also, the diameter of passageway 20 could also be made to accommodate a needle, hollow cannula or pipette especially in instances where small quantities of liquid are to be handled.

At the opposite end of the housing, there is another protrusion 22 including an internally tapered wall surface 24 defining a passageway 25 extending therethrough and terminating in an opening 26. Opening 26 thereby provides fluid communication between passageway 25 and chamber 18. Passageway 25 is preferably wider than passageway 20 at the other end of the housing, and thereby provides a wide mouth portion for receiving a mating portion, such as from a syringe or other device which will provide a driving force for aspirating liquid into and injecting liquid out of the hub device. An annular flange 28 surrounds this projecting portion and facilitates the grasping of the hub device during, for example, its attachment to a syringe. Although it is not necessary for the purposes of the present invention, it is preferred that openings 21 and 26 be on opposite sides of the housing, astride the chamber within, and also in substantial alignment with each other along the longitudinal axis of the device.

Turning to the specifics of valve 14, it is preferably a tubular member, flexible in nature and relatively elongate in appearance. Both ends of this valve have operable valve closure elements thereon: a first valve element 30 and a second valve element 31. The first valve element is positioned directly over opening 21 and includes flexible arms 32 extending downwardly toward the wall of the housing. As can be seen in FIG. 2, flexible arms 32 need be no more than a finely tapered circumferential portion of the tubular valve which circumscribes opening 21. In the normal rest or static condition, this flexible wall portion of the tubular valve remains substantially straight so that the interior 34 of the tubular valve is in fluid communication with opening 21.

On the other hand, the second valve element on the opposite end of the valve remains closed during the normal rest or static conditions. Specifically, second valve element 31 includes flexible flaps 35 with a small slot 36 therebetween. These flaps are adapted to normally close against the slot and to remain closed under static conditions, or if a force external to the flaps is applied, such as liquid flowing against the outside surfaces of these flaps. This configuration of this type of valve element as illustrated herein is commonly referred to as a "duckbill" valve, whose operation is very well known.

In the preferred embodiment being discussed, filter element 16 serves two purposes: it filters particulate matter, including bacteria when the pore rating is low enough, from liquids passing therethrough while also serving as a support member in order to maintain valve 14 in position inside the chamber. In this instance, filter 16 is a cylindrical disk or plug of material sufficiently porous to allow liquid to pass therethrough while at the same time collecting particulate matter which may be present in the liquid. The pore rating of the filter is generally left to the choice of the operator to suit the particular needs and circumstances in which the hub device is being employed. Use of a filter with a 0.2 micron pore rating will allow the filtration of bacteria from the liquid. As can be seen in FIG. 2, filter 16 includes a substantially centrally located hole 38 into which valve 14 is desirably press fit. An annular tab 39 around the valve cooperates in maintaining the valve securely positioned in the chamber by the supporting features of filter 16.

It is appreciated that other filters and supporting elements for the valve, if necessary, fall within the purview of the present invention. One alternate construction is illustrated in FIG. 3. Valve 14a is supported within chamber 18a by a cylindrical plug 17 of generally porous material so that liquid can readily pass through this material. Some filtration by this porous material may occur when the liquid travels through this material. The prime filtration element in this embodiment is, however, a thin porous membrane 16a which extends across chamber 18a and is supported on the cylindrical plug. Once again, the pore rating of the thin porous membrane is usually left to the choice of the operator. The filtration aspects of the embodiment of FIG. 3 operate essentially the same as those of the embodiment of FIGS. 1 and 2, which can be more fully appreciated by now referring to FIGS. 4 and 5.

With particular reference to FIG. 4, hub device 10 is illustrated in its appearance during aspiration of liquid from a source 40. During this aspiration procedure, extension 19 is conveniently placed in the source of liquid so that passageway 20 is in communication with the liquid. Of course, various attachments may be made to extension 19 in order to tap into the source of liquid. At the other end of hub device 10, a syringe 41 or other device is connected to the hub device by virtue of a tapered male connector 42 mated into the passageway of the wider mouth portion. During aspiration, the syringe barrel (not shown) is normally withdrawn outwardly to create a suction effect and a negative pressure inside the syringe. As a result, this negative pressure gradient is applied inside chamber 18 of the housing. This negative pressure gradient causes flexible flaps 35 to move away from and open slot 36. As soon as slot 36 opens, the negative pressure gradient of the aspiration step draws liquid from source 40 through passageway 20 and into interior 34 of the valve, whereupon it travels through open slot 36 and wider opening 26 and then into the syringe where it is collected. When the liquid enters the interior of the valve, it causes a radially outward force against flexible arms 32 thereby pushing these flexible arms tightly, in a radially outward direction, against filter plug 16, thereby serving as a valve closure mechanism. The preferred thin nature of flexible arms 32 can be aligned so that they cause a wiping action against the bottom wall of the housing to prevent leakage of the liquid at the interface between flexible arms and the housing wall. Thus, during aspiration, filter 16 has no liquid passing through it so that it does not become contaminated due to the fact that the closed valve prevents liquid from passing in the direction through the filter.

Figure 5:
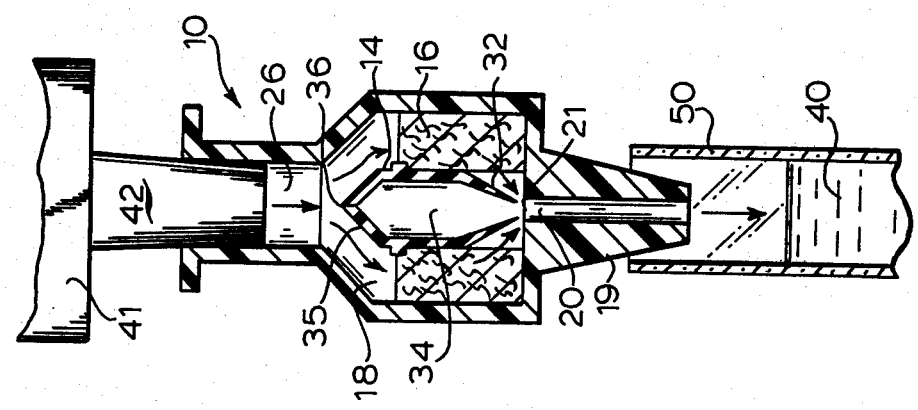
FIG. 5 is a cross-sectional view of the hub device of FIG. 1 illustrating its use during the injection step in conjunction with the same syringe as in FIG. 4.

Turning now to FIG. 5, hub device 10 is illustrated as still being connected to syringe 41. Of course, the liquid collected from source 40 is, at this time, in the barrel of the syringe. This collected liquid may now be conveniently injected into another location, such as a different container 50, without the need to remove the hub device from the syringe. Once injection of the collected liquid is initiated by depression of the plunger of the syringe (not shown) the force of the injected liquid causes its movement through wider opening 26 into chamber 18. Although flexible flaps 35 normally close against slot 36 in the rest condition, this flow of liquid against the exterior surfaces of these flaps causes an additional tightening or closing effect to thereby prevent liquid from flowing into interior 34 of the valve. Accordingly, liquid is diverted around the valve and passes through porous filter 16, whereby the liquid is filtered of particulate matter which may be present in the liquid (within the pore rating of the filter material). Passage of the liquid through the chamber and filter toward opening 21 causes flexible arms 32 to be deflected inwardly to provide a direct liquid communication between chamber 18 and opening 21. Liquid then readily flows through the filter, then through a portion of chamber 18 surrounding and exterior to the inwardly deflected arms 32, through opening 21 and ultimately into collection container 50.

While FIG. 4 illustrates the hub device of the present invention in an aspiration mode and FIG. 5 illustrates the same hub device in an injection mode, it is appreciated that the directions connoted by aspiration and injection are merely illustrative. Accordingly, with the appropriate connecting elements, the roles illustrated in FIGS. 4 and 5 can be reversed whereupon FIG. 4 would represent an injection mode and FIG. 5 an aspiration mode. In this event, the filtration of the liquid would occur during the aspiration of the liquid from the first source or location.

While many materials may be selected for the various elements of the present invention, it is preferred that the housing and connected external components be made of plastic, such as polycarbonate. On the other hand, the flexible valve of the present invention is preferably made of an elastomeric material, such as silicone rubber. One type of filter material which is suitable for the present invention is porous acrylic copolymer.

This, the present invention provides a hub device particularly useful in aspirating and injecting liquids, which can remain attached to a syringe or like device during both aspiration and injection steps. Furthermore, isolation of the filter of this hub device is provided during the passage of liquid through the device in one direction, while the filter comes into effect during flow of the liquid through the hub device in the opposite direction. The aspiration/injection procedure for transferring liquids thus becomes greatly simplified.

What is claimed is:

1. A hub device for use in aspirating and injecting liquids comprising:

a housing having a chamber therein, a first opening for aspirating liquid into the chamber and for injecting liquid out of the chamber and a second opening extending through a mouth portion which is adapted to connect to a mating portion of a liquid movement device which serves as a driving force for aspirating liquid into and injecting liquid out of said device, said openings being located on opposite sides of said housing in substantially axial alignment with each other;

a tubular valve in said chamber having a flexible, operable closure element on opposite ends thereof; and a filter in said chamber adapted to filter particulate matter from liquids passing therethrough, said filter also serving as a support member to maintain said valve in position in said chamber, said filter surrounding said valve including the first operable closure element thereof, said first element of said valve being positioned directly over said first opening and normally closing radially outwardly against said surrounding filter in an orientation substantially parallel to the axial alignment of said openings so that the interior of said tubular valve is in liquid communication with said first opening whereby liquid flowing through said first opening during aspiration is directed through said tubular member, said first element adapted to flexibly move away from said filter to thereby open and place said first opening in liquid communication with the chamber exterior to said tubular valve during injection of liquid into the chamber through said second opening, said second element including an operable slot adapted to open during aspiration of liquid inwardly through said first opening and normally close under static conditions and remain closed upon injection of liquid into said chamber through said second opening.

* * * * *